United States Patent [19]

Cartwright et al.

[11] 4,246,419
[45] Jan. 20, 1981

[54] HERBICIDAL COMPOUNDS

[75] Inventors: David Cartwright, Reading; Roger Salmon, Bracknell, both of England

[73] Assignee: Imperial Chemical Industries Limited, London, England

[21] Appl. No.: 9,361

[22] Filed: Feb. 5, 1979

[30] Foreign Application Priority Data

Feb. 15, 1978 [GB] United Kingdom ............. 6043/78

[51] Int. Cl.³ .................................. C07D 213/64
[52] U.S. Cl. ...................... 546/291; 71/94; 71/92; 71/103; 544/316; 564/97; 564/99
[58] Field of Search ........................... 546/291

[56] References Cited

U.S. PATENT DOCUMENTS

| 3,622,626 | 11/1971 | Moore | 71/103 |
| 4,115,102 | 9/1978 | Takahashi et al. | 546/291 |

FOREIGN PATENT DOCUMENTS

| 2277811 | 2/1976 | France. |
| 2288089 | 5/1976 | France. |
| 2398059 | 2/1979 | France. |
| 7804851 | 11/1978 | Netherlands. |
| 1491274 | 11/1977 | United Kingdom. |
| 1519334 | 7/1978 | United Kingdom. |
| 2014565 | 8/1979 | United Kingdom. |

*Primary Examiner*—John M. Ford
*Attorney, Agent, or Firm*—Cushman, Darby & Cushman

[57] ABSTRACT

A herbicidal sulphonamide compound of the formula (I):

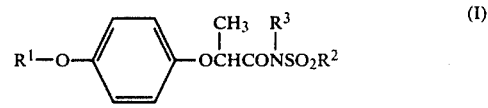

and salts thereof, wherein $R^1$ is a pyridyl group of the formula:

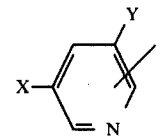

wherein the group X of the pyridyl group represents a fluorine, chlorine, bromine, or iodine atom, or an alkyl radical of 1 to 4 carbon atoms optionally substituted by one or more fluorine or chlorine atoms, and the group Y represents hydrogen, fluorine chlorine, bromine, or iodine or an alkyl radical of 1 to 4 carbon atoms optionally substituted by one or more fluorine or chlorine atoms; $R^2$ represents an alkyl radical of 1 to 6 carbon atoms optionally substituted by one or more fluorine atoms; and $R^3$ is hydrogen or an alkyl radical of 1 to 4 carbon atoms.

4 Claims, No Drawings

HERBICIDAL COMPOUNDS

This invention relates to chemical compounds having herbicidal properties, and to herbicidal compositions and processes utilising these compounds.

According to the present invention there are provided herbicidal sulphonamide compounds of the formula (I):

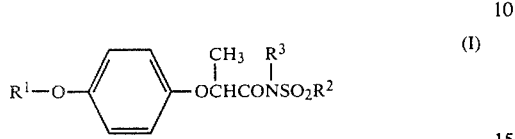

or a tautomer thereof, and salts thereof, wherein $R^1$ is a pyridyl group of the formula:

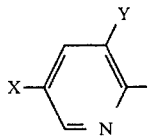

or a phenyl group of the formula:

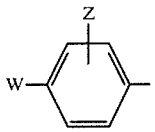

or a pyrimidinyl group of the formula:

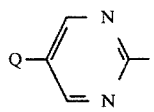

wherein the group X of the pyridyl group represents a fluorine, chlorine, bromine, or iodine atom, or an alkyl radical of 1 to 4 carbon atoms optionally substituted by one or more fluorine or chlorine atoms, and the group Y represents hydrogen, fluorine, chlorine, bromine, or iodine, or an alkyl radical of 1 to 4 carbon atoms optionally substituted by one or more fluorine or chlorine atoms; the group W of the phenyl group represents a fluorine, chlorine, bromine, or iodine atom, or a trifluoromethyl group; the group Z represents a hydrogen atom or one or more fluorine; chlorine, bromine, or iodine atoms; the group Q represents a fluorine, chlorine, bromine, or iodine atom or a trifluoromethyl group; $R^2$ represents an alkyl radical of 1 to 6 carbon atoms optionally substituted by one or more fluorine atoms; and $R^3$ is hydrogen or an alkyl radical of 1 to 4 carbon atoms.

Examples of compounds within the scope of the invention include those in which the group $R^1$ is 3,5-dichloro-2-pyridyl; 5-chloro-2-pyridyl; 3-chloro-5-trifluoromethyl-2-pyridyl; 5-trifluoromethyl-2-pyridyl; 4-trifluoromethylphenyl; 2-chloro-4-trifluoromethylphenyl; 4-chlorophenyl; or 2,4-dichlorophenyl. The group $R^2$ is preferably an alkyl radical of 1 to 4 carbon atoms, for example a methyl radical. When $R^2$ is an alkyl radical substituted by fluorine it may for example be a trifluoromethyl radical.

It will be appreciated that the compounds of formula (I) possess an asymmetric carbon atom and may therefore exist in racemic and optically active forms.

Particular examples of compounds according to the invention are listed in Table I.

TABLE I

| COMPOUND NO | $R^1$ | $R^2$ | $R^3$ | MELTING POINT °C. |
|---|---|---|---|---|
| 1 | 3,5-dichloro-2-pyridyl | $CH_3$ | H | 141–142 |
| 2 | 3,5-dichloro-2-pyridyl | $C_4H_9$ | H | 134–135 |
| 3 | 4-trifluoromethyl phenyl | $CH_3$ | H | 118–119 |
| 4 | 4-trifluoromethyl phenyl | $C_4H_9$ | H | 96–97 |
| 5 | 4-chlorophenyl | $CH_3$ | H | 110–111 |
| 6 | 5-trifluoromethyl-2-pyridyl | $CH_3$ | H | 142–142.5 |
| 7 | 3-chloro-5-trifluoromethyl-2-pyridyl | $CH_3$ | H | 104–105 |
| 8 | 5-trifluoromethyl-2-pyridyl | $C_2H_5$ | H | 118–119 |
| 9 | 5-trifluoromethyl-2-pyridyl | $C_3H_7$ | H | 87–89 |
| 10 | 5-trifluoromethyl-2-pyridyl | iso-$C_3H_7$ | H | 106–107 |
| 11 | 5-trifluoromethyl-2-pyridyl | $C_4H_9$ | H | 89–91 |
| 12 | 5-trifluoromethyl-2-pyridyl | $C_6H_{13}$ | H | 94–95 |
| 13 | 5-trifluoromethyl-2-pyridyl | $CH_3$ | $CH_3$ | oil |
| 14 | 3-chloro-5-chlorodifluoromethyl-2-pyridyl | $CH_3$ | H | 89–90 |
| 15 | 5-iodo-2-pyrimidinyl | $CH_3$ | H | 167–169 |

Further examples of compounds falling within the scope of the invention include the following:

N-methanesulphonyl-2[4-(5-difluoromethyl-2-pyridyloxy)-phenoxy]propionamide (formula I, $R^1$=5-difluoromethyl-2-pyridyl, $R^2$=$CH_3$ and $R^3$=H).

N-methanesulphonyl-2[4-(3-chloro-5-difluoromethyl-2-pyridyloxy)phenoxy]propionamide (formula I, $R^1$=3-chloro-5-difluoromethyl-2-pyridyl, $R^2$=$CH_3$ and $R^3$=H).

N-methanesulphonyl-2[4-(3,5-bis-trifluoromethyl-2-pyridyloxy)phenoxy]propionamide (formula I, $R^1$=3,5-bis-trifluoromethyl-2-pyridyl, $R^2$=$CH_3$ and $R^3$=H).

N-methanesulphonyl-2[4-(3-bromo-5-trifluoromethyl-2-pyridyloxy)phenoxy]propionamide (formula I, $R^1$=3-bromo-5-trifluoromethyl-2-pyridyl, $R^2$=$CH_3$ and $R^3$=H).

N-methanesulphonyl-2[4-(5-difluorochloromethyl-2-pyridyloxy)phenoxy]propionamide (formula I, $R^1$=5-difluorochloromethyl-2-pyridyl, $R^2$=$CH_3$ and $R^3$=H).

N-methanesulphonyl-2[4-(5-trifluoromethyl-2-pyrimidinyloxy)-phenoxy]propionamide (formula I, $R^1$=5-trifluoromethyl-2-pyrimidinyl, $R^2$=$CH_3$ and $R^3$=H).

N-methanesulphonyl-2[4-(5-iodo-2-pyridyloxy)phenoxy]-propionamide (formula I, $R^1$=5-iodo-2-pyridyl, $R^2$=$CH_3$ and $R^3$=H).

N-methanesulphonyl-2[4-(5-bromo-2-pyrimidinyloxy)-phenoxy]propionamide (formula I, $R^1$=5-bromo-2-pyrimidinyl, $R^2$=$CH_3$ and $R^3$=H).

Compounds of the invention wherein the group $R^3$ is a hydrogen atom are acids and form salts with bases. Both the acid and the salt forms of the compounds may be used as herbicides. Examples of salts include metal salts and salts formed from ammonium and substituted ammonium cations. Among the metal salts are those in which the metal cation is an alkali metal cation, for example sodium, potassium, or lithium or an alkaline earth metal cation, for example calcium or magnesium. The substituted ammonium cation include mono-, di-, tri- and tetra-substituted ammonium cations in which the substituents may be for example an alkyl or alkenyl radical of 1 to 20 carbon atoms optionally containing one or more hydroxy, alkoxy or phenyl substituents. Particular examples of substituted ammonium cations include isopropylammonium, triethanolammonium, benzyltrimethylammonium, morpholinium, piperidinium, trimethylammonium, triethylammonium, methoxyethylammonium, dodecylammonium and octadecylammonium.

The compounds of the invention are herbicides which are in general substantially more effective against grass species than against broad-leaved species of plant. They may be used to control unwanted grass species growing alone, or at suitable rates of application they may be used to control grass weeds growing among broad-leaved crop plants. The compounds may be either applied to the soil before the emergence of the unwanted grass species (pre-emergence application) or to the above-ground parts of growing grass plants (post-emergence application).

In another aspect, therefore, the invention provides a process of inhibiting the growth of unwanted plants, particularly grass species, which comprises applying to the plants, or to the locus thereof, a herbicidally effective amount of a compound of formula (I) as hereinbefore defined.

The amount of the compound to be applied will depend upon a number of factors, for example the particular plant species whose growth is to be inhibited, but in general an amount of from 0.1 to 5 kilograms per hectare is usually suitable. The skilled worker in the art will readily be able to determine suitable amounts for use by means of standardised routine tests, without undue experimentation.

The compounds of the invention are preferably applied in the form of compositions, in which the active ingredient is mixed with a carrier comprising a solid or liquid diluent. Preferably the composition further comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl and triiso-propylnaphthalenesulphonic acid. Suitable agents of the non-ionic type include, for example, the condensation products of ethylene oxide with fatty alcohols such as oleyl alcohol and cetyl alcohol, or with alkyl phenols such as octyl-phenyl, nonylphenol, and octylcresol. Other non-ionic agents are the partial esters derived from long chain fatty acids and hexitol anhydrides, for example sorbitol mono-laurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment. In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The compounds of the invention may be prepared by the route outlined in Scheme A below:

SCHEME A

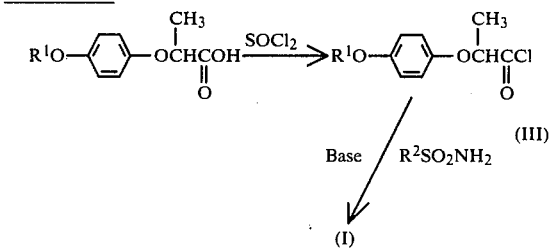

In Scheme A, an appropriately substituted carboxylic acid (II) is converted by a chlorinating agent, for example thionyl chloride, to the corresponding acid chloride (III). This acid chloride is then reacted with the appropriate sulphonamide $R^2SO_2NH_2$ in the presence of a base to give the required compounds (I). The base used in the reaction to obtain (I) may be a tertiary amine, for example dimethylaniline or pyridine. The reaction is carried out at an elevated temperature, for example at a temperature of 50° C. or above. Conveniently the reaction is conducted at a temperature in the range from 50° to 150° C.

Conveniently, an excess of the tertiary amine over the stoichiometric amount required to react with the hydrogen chloride formed in the reaction may be used, so as to provide a solvent or diluent for the reactants. When pyridine is used as a solvent, the reaction may be done at the boiling point (115°–116° C.) of pyridine. Alternatively, the stoichiometric amount of amine may be used, together with a solvent or diluent if desired. Examples of solvents or diluents include toluene.

The compounds (I) may be isolated from the reaction mixture by conventional methods. If a solvent or diluent is present, it may be removed under reduced pressure. The residue comprising the required compound and the amine hydrochloride may be mixed with water and acidified, and the product extracted with a water-immiscible solvent, for example with ether or chloroform, and then recovered by evaporation of the solvent.

The carboxylic acids used as starting materials in Scheme A are for the most part known. Where not already known, they may be prepared by methods analogous to those used to prepare the known compounds.

Thus, in general, the carboxylic acids required as starting materials for Scheme A may be prepared as outlined in Scheme B below.

SCHEME B

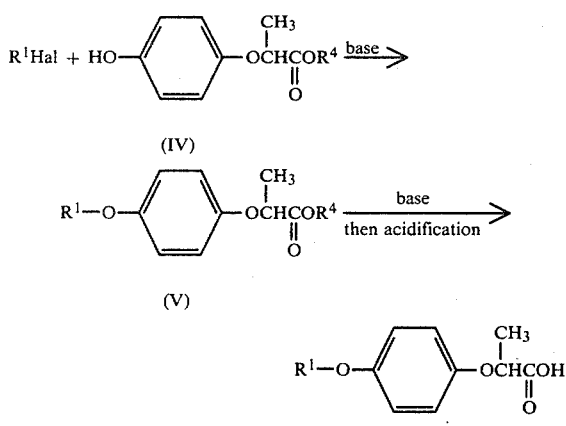

(IV)

(V)

In Scheme B, $R^1$ has the meaning previously assigned to it, Hal represents a halogen, for example chlorine or bromine, and $R^4$ is an esterifying radical, which may conveniently be an alkyl group of 1 to 6 carbon atoms, for example a methyl or ethyl radical.

In Scheme B, the halogeno compound $R^1$Hal is reacted with the phenolic derivative (IV) in the presence of a base to give the required carboxylic acid in the form of an ester thereof. Preferably the reaction is carried out in a solvent or diluent for the reactants. The base may be for example an alkali metal carbonate, for example anhydrous potassium carbonate or sodium carbonate. Examples of solvents include ketones, for example acetone or methyl ethyl ketone. The reaction may be accelerated by heating for example to the reflux temperature of the solvent. The product may be isolated by conventional procedures for recovery of organic compounds from reaction mixtures.

The esters (IV) obtained by the above reaction may be hydrolysed to the corresponding carboxylic acids by conventional methods. The ester may for example be stirred at room temperature in an aqueous alcoholic solution with a molar amount of an alkali metal hydroxide, for example sodium or potassium hydroxide. Hydrolysis of the ester in this way provides the required carboxylic acid in the form of a metal salt. The free acid may be obtained from the reaction mixture by conventional means; for example, the mixture may be acidified and extracted with a water-immiscible solvent, and the carboxylic acid recovered from the extract.

It will be apparent to those skilled in the art that alternative processes for preparing the compounds of the invention may be visualised. One such process is outlined in Scheme C.

SCHEME C

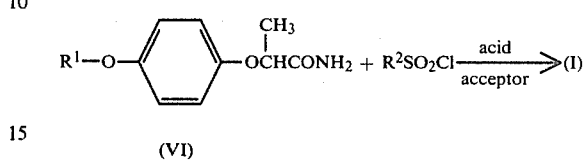

(VI)

In Scheme C, the symbols $R^1$ and $R^2$ have the meanings previously assigned to them. The acid acceptor may be, for example, a tertiary amine, for example pyridine or dimethylaniline. The reaction may be carried out under conditions similar to those described for the process of Scheme A. The amides (VI) required as starting materials for Scheme C may be obtained for example, by reaction of the acid chlorides (III) with ammonia according to conventional methods.

Further processes for preparing the compounds of the invention are outlined in Scheme D.

SCHEME D

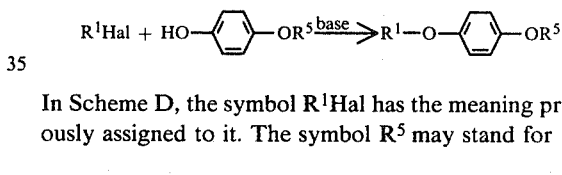

In Scheme D, the symbol $R^1$Hal has the meaning previously assigned to it. The symbol $R^5$ may stand for

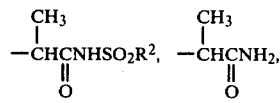

a $C_1$ to $C_4$ alkyl group, or a hydrogen atom.

When $R^5$ stands for the group

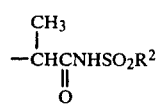

the product of the reaction is a compound according to the invention. When $R^5$ stands for the group

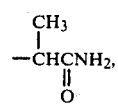

the product of the reaction is an amide (VI) which can be converted into a compound of the invention by the process of Scheme C.

When $R^5$ stands for a $C_1$ to $C_4$ alkyl group, the product of the reaction is an alkyl ether of formula (VII) wherein $R^6$ is an alkyl group of 1 to 4 carbon atoms.

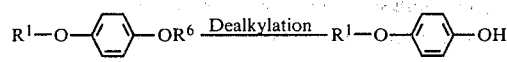

(VII)   (VIII)

The alkyl ester (VII) may be dealkylated by standard methods, for example treatment with pyridine hydrochloride or boron tribromide, to give the phenol derivative (VIII). This may then be reacted with a 2-chloro or 2-bromopropionic acid derivative of formula:

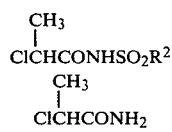

to give, respectively, either a compound of the invention directly, or an amide (VI) which may be converted to a compound of the invention by the process of Scheme C.

When $R^5$ stands for a hydrogen atom, the product of the reaction outlined in Scheme D will be a phenolic derivative (VIII) which may be converted to a compound of the invention by the processes outlined in the last foregoing paragraph. When $R^5$ is a hydrogen atom, there is a likelihood that the process outlined in Scheme D will produce a proportion of by-product of formula

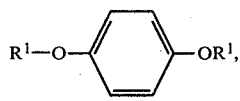

arising from reaction of two molecules of the halogeno compound $R^1Hal$ with hydroquinone; however this may be readily separated by conventional methods from the required phenolic derivative (VIII).

The above description of processes for preparing the compounds of the invention relates only to preparation of compounds wherein $R^3$ is a hydrogen atom. Compounds wherein $R^3$ is an alkyl group of 1 to 4 carbon atoms may be prepared for example by reaction of the appropriate diazoalkane with a compound of the invention wherein $R^3$ is a hydrogen atom, according to conventional procedures known for such reactions.

The invention is illustrated by the following Examples, in which all parts are by weight and all temperatures are in degrees Centigrade unless otherwise stated. The expression NMR spectrum means nuclear magnetic resonance spectrum.

EXAMPLE 1

This Example describes the preparation of N-methanesulphonyl α-[4(3,5-dichloropyridyl-2-oxy)-phenoxy]propionamide (compound no 1 of Table I).

α-[4(3,5-dichloropyridyl-2-oxy)phenoxy]propionic acid (1.5 g) was heated under reflux with thionyl chloride (20 ml) for 2 hours. The excess of thionyl chloride was removed in a vacuum, and finely powdered methanesulphonamide (0.50 g) was added. Pyridine (dry, 10 ml) was added and the mixture heated at 100° C. for 30 minutes. The pyridine was removed under vacuum, and the residue diluted with water and acidified with 2-molar hydrochloric acid. The tarry solid which separated was washed with water and taken up in chloroform (100 ml). The chloroform solution was dried and evaporated. The residue was triturated with ether to give a solid with a melting point of 141°–142° C. identified as compound no 1 of Table I.

Following the same procedure but using butanesulphonamide in place of methanesulphonamide, compound no 2 of Table I was prepared; in this case the product was purified by trituration with petroleum (b.p. 40°–60° C.) and a little ether, and recrystallised from a mixture of toluene with petroleum (b.p. 80°–100° C.).

EXAMPLE 2

This Example describes the preparation of N-methanesulphonyl α-[4-(4-trifluoromethylphenoxy)-phenoxy]propionamide (compound no 3 of Table I).

α-[4(4-trifluoromethylphenoxy)phenoxy]propionic acid (2.5 g) was stirred and heated to reflux with thionyl chloride (25 ml) for 3 hours. The excess of thionyl chloride was removed under a vacuum. The residue was dissolved in dry pyridine (25 ml) and methanesulphonamide (0.76 g) added. The mixture was heated under reflux for 2 hours, and the pyridine then removed in a vacuum. The residue was extracted with water and ether. The mixture of water and ether was acidified with 2-molar hydrochloric acid and salt added to assist in separating the ether layer. The ether extract was dried and evaporated. The residue was triturated with a mixture of petroleum and ether to give a solid. This was recrystallised from isopropanol to give compound no 3 of Table I, with a melting point of 118°–119° C.

Following the same procedure, but using butanesulphonamide instead of methanesulphonamide, compound no 4 of Table I was obtained. In this case the product was purified by placing it in a Soxhlet extractor and extracting it with petroleum. The extracts deposited compound no 4 on cooling.

EXAMPLE 3

This Example illustrates the preparation of N-methanesulphonyl α-[4-(4-chlorophenoxy)phenoxy]-propionamide (compound no 5 of Table I).

α-4-(4-chlorophenoxy)phenoxypropionic acid (1.0 g) was mixed with thionyl chloride (12 ml), and stirred and heated under reflux for 2 hours. The excess of thionyl chloride was removed under reduced pressure. The remaining oil was taken up in dry pyridine (10 ml) and methanesulphonamide (0.32g) added. The mixture was heated on the steam-bath with stirring for 3 hours. The pyridine was removed under reduced pressure and the residue acidified with hydrochloric acid (2 M). The solution was extracted with ether (300 ml). The ether extract was washed with a little water, dried, and evaporated to give a sticky solid. Recrystallisation from petroleum (b.p. 80°–100° C.) containing a little toluene gave a colourless solid identified as compound no 5, with a melting point of 110°–111° C.

EXAMPLE 4

This Example illustrates the preparation of N-methanesulphonyl α-[4-(5-trifluoromethylpyridyl-2-oxy)phenoxy]propionamide (compound no 6 of Table I).

(a) Preparation of 2-chloro-5-trichloromethylpyridine

2-Bromo-5-methylpyridine (27 g) in dry carbon tetrachloride (500 ml) was treated with dry hydrogen chloride to give the hydrochloride salt. The solid which separated was broken up and the mixture heated to reflux. Chlorine was passed through the boiling mixture for 8 hours with irradiation by an ultra-violet lamp. The mixture was then filtered and evaporated to a pale yellow liquid which solidified on cooling. This was identified as the required chloro compound by its nuclear magnetic resonance spectrum.

(b) Preparation of 2-chloro-5-trifluoromethylpyridine and 2-chloro-5-difluorochloromethylpyridine The product from (a) (18 g) and antimony trifluoride (50 g) were heated together at 140°-145° C. for 1 hour. The mixture was cooled, mixed with ice and concentrated hyrochloric acid, and extracted with ether. The extracts were washed with water, dried with magnesium sulphate, and evaporated. The products from several such preparations were combined and distilled at atmospheric pressure through a short column packed with Fenske rings. The product boiling at 124°-154° C. was collected and identified as 2-chloro-5-trifluoromethylpyridine. Higher boiling fractions wee redistilled at a pressure of 20 mm mercury to give 2-chloro-5-difluorochloromethylpyridine, boiling at 82° to 90° C.

(c) Preparation of 2-p-methoxyphenoxy-5-trifluoromethylpyridine

The product from (b) boiling at 124°-154° C. (1.82 g) was added in dry dimethylsulphoxide (15 ml) to a solution of p-methoxyphenol (1.24 g) in dimethylsulphoxide (20 ml) previously reacted with sodium hydride (0.48 g of a 50:50 oil dispersion). The mixture was stirred and heated to 60° to 65° for 5 hours, poured into ice, and extracted with ether. The ether extracts gave an oil.

(d) Preparation of 2-p-hydroxyphenoxy-5-trifluoromethylpyridine

The product from (c) (1.7 g) and excess of pyridine hydrochloride were heated together for 8 hours at 180° C. The mixture was cooled, diluted with water and 2-molar hydrochloric acid, and extracted with ether. The extracts were dried and evaporated to yield an oil identified as the required hydroxy compound.

(e) Preparation of ethyl α-[4-(5-trifluoromethyl pyridyl-2-oxy)phenoxy]propionate The product from (d) (0.22 g), ethyl α-bromopropionate (0.24 g) and potassium carbonate (0.18 g) in methyl ethyl ketone (5 ml) were stirred, and heated under reflux for 2 hours. The mixture was left to cool overnight, then filtered, and the residue washed with methyl ethyl ketone. The filtrate and washings were evaporated and the remaining oil subjected to a high vacuum to remove traces of solvent. The nuclear magnetic resonance spectrum of the oil was consistent with the structure assigned and the compound was identified as the required ester.

(f) Preparation of α-[4-(5-trifluoromethylpyridyl-2-oxy)phenoxy]propionic acid

The product from (e) (0.14 g) is isopropanol (2 ml) was stirred at room temperature for 1¾ hours with an aqueous solution of sodium hydroxide (1.6 ml of a solution containing 1 g NaOH per 100 ml water). The mixture was evaporated in a vacuum and the residue taken up in water, acidified, and extracted with ether (2×50 ml). The ether extracts yielded an oil identified as the required carboxylic acid.

(g) Preparation of compound no 6

The product (1.2 g) from a preparation carried out as in paragraph (f), but on a larger scale, was heated under reflux in thionyl chloride (20 ml) for 2 hours. The excess of thionyl chloride was removed under reduced pressure. The yellow oil which remained was taken up in pyridine (20 ml) and a solution of methanesulphonamide (0.5 g) in pyridine (5 ml) added. The mixture was heated on the steambath for 2 hours, and the pyridine then removed under reduced pressure. Toluene was added and evaporated off under reduced pressure. The residue was taken up in chloroform and the solution washed successively with water, hydrochloric acid (2 M) and water. The chloroform solution was dried and evaporated to give a solid. Recrystallisation from a mixture of ethyl acetate and petroleum (b.p. 40°-60° C.) gave the sulphonamide (compound no 6) as an off-white powder with a melting point of 142°-142.5° C.

In a further preparation, the product (9 g) obtained from a preparation as described in paragraph (f), but on a larger scale, was heated under reflux in thionyl chloride (150 ml) with stirring for 3 hours. The mixture was cooled and the excess of thionyl chloride removed in a vacuum. The residue solidified on cooling in ice. The acid chloride so obtained (3.2 g) and methanesulphonamide (0.87 g) were stirred and heated under reflux in pyridine (40 ml) for 10 hours. The pyridine was removed under reduced pressure and the residue mixed with ice and acidified with 2 molar hydrochloric acid. A solid separated. The mixture was extracted with ether (2×200 ml) and the ether extracts dried and evaporated to give a solid which was washed with petroleum (b.p. 30°-40° C.). The solid (2.9 g) so obtained was recrystallised from a mixture of ethyl acetate and petroleum (b.p. 60°-80° C.) and identified as compound no 6 of Table I by elemental analysis, and its NMR and mass spectra.

EXAMPLE 5

This Example illustrates the preparation of compound no 7 of Table I, that is to say, N-methanesulphonyl α-[4-(3-chloro-5-trifluoromethylpyridyl-2-oxy)-phenoxy]-propionamide.

(a) Preparation of 2-amino-3-bromo-5-methylpyridine

2-Amino-5-methylpyridine (108 g) in glacial acetic acid (300 ml) was heated to 90°-100° C. while bromine (160 g) in acetic acid (55 ml) was slowly added with stirring. When addition was complete, the mixture was stirred and heated for a further 30 minutes and then allowed to cool overnight. The solid which separated was filtered off and mixed with ice and the mixture neutralised with concentrated ammonia, keeping the temperature at 0° to 5° C. The solid was collected, washed with water, and dried to give the bromo-compound.

(b) Preparation of 3-bromo-2-chloro-5-methylpyridine

The product from (a) (145 g) was dissolved in concentrated hydrochloric acid (750 ml) and water (450 ml) and the solution cooled to −10° C. Sodium nitrite (54 g) in cold water (450 ml) was added dropwise with stirring over a period of 90 minutes while the mixture was kept at 5° C. The solution was stirred for a further 2 hours, and then basified with concentrated ammonia, keeping the temperature below 20° C. The solid which separated was washed with water, dried, dissolved in ether (1500 ml) and washed with cold sodium hydroxide solution (1 M; 1 liter). The ether solution was washed twice with water (1 liter portions), dried, and evaporated to give the required 3-bromo-2-chloro-5-methylpyridine.

(c) Preparation of 2,3-dichloro-5-trichloromethylpyridine

The product from (b) (64 g) in dry carbon tetrachloride (650 ml) was treated with dry hydrogen chloride. The precipitate was broken up and the suspension heated under reflux while dry chlorine was bubbled into the mixture, with illumination from an ultra-violet light source. After 4½ hours, the mixture was cooled, filtered, and the filtrate evaporated to give the required 2,3-dichloro-5-trichloromethylpyridine. The mass spectrum was consistent with the structure assigned to this compound.

(d) Preparation of 2,3-dichloro-5-trifluoromethylpyridine

The product from (c) (1.0 g) and antimony trifluoride (3.0 g) were heated together at 170°–180° for 30 minutes. The mixture was then cooled, mixed with ice and water, and extracted with ether. The ether extracts gave a brown oil containing a mixture of 2,3-dichloro-5-trifluoromethylpyridine and 3-chloro-2-fluoro-5-trifluoromethylpyridine with a minor amount of 2,3-dichloro-5-chlorodifluoromethylpyridine.

(e) Preparation of 3-chloro-2-p-methoxyphenoxy-5-trifluoromethylpyridine p-Methoxyphenol (1.5 g) was added to a suspension of sodium hydride (0.6 g 50% oil dispersion, washed with petroleum) in dry dimethyl sulphoxide (30 ml) and the mixture stirred for 15 minutes. A solution of the combined products (1.5 g) from several preparations carried out as described in paragraph (d), in dimethylsulphoxide (20 ml) was added to the reaction mixture and heated to 60° C. for four hours. A further amount of sodium hydride (0.3 g of 50% oil dispersion, washed with petroleum), and potassium carbonate (1.38 g) was added. Heating was continued for another 4 hours. The mixture was poured into ice and water, and extracted with ether (400 ml). The ether extracts were washed with water, dilute sodium hydroxide, and water, dried, and evaporated to give the product.

(f) Preparation of 3-chloro-2-p-hydroxyphenoxy-5-trifluoromethylpyridine

The product from (e) (2 g) was heated with pyridine hydrochloride (20 g) at 170°–180° C. for 6 hours. The mixture was cooled, diluted with dilute hydrochloric acid, and extracted with ether. The ether extracts gave an oily solid which was purified by preparative thin layer chromatography using silica as the adsorbent and 6% ethanol-chloroform as the solvent.

(g) Preparation of ethyl α-[4-(3-chloro-5-trifluoromethylpyridyl-2-oxy)phenoxy]propionate The product from (f) (0.16 g), ethyl alpha bromopropionate (0.3 g), and potassium carbonate (0.25 g) were heated and stirred under reflux in methyl ethyl ketone (10 ml) for 2 hours. The mixture was cooled and filtered. Evaporation of the filtrate gave an oil which was heated in a vacuum to remove traces of solvent. The oil was identified as the required ester by examination of its mass spectrum and its purity was confirmed by gas-liquid chromatography.

(h) Preparation of α-4(3-chloro-5-trifluoromethylpyridyl-2-oxy)phenoxypropionic acid The product (1.80 g) from (g), repeated on a larger scale, was dissolved in isopropanol (20 ml) and treated dropwise at room temperature with sodium hydroxide solution (18.4 ml of a solution of 1 g sodium hydroxide in 100 ml water). The mixture was stirred at room temperature for 1.5 hours.

The solution was then concentrated under reduced pressure and then diluted with water to 130 ml. The solution was acidified with dilute hydrochloric acid and extracted with chloroform (3×200 ml). The chloroform extracts gave a colourless oil which partially solidified on storage; this was identified as the required acid.

(i) Preparation of compound no 7

The product from (h) (1.7 g) was stirred under reflux in thionyl chloride (25 ml) for 1.5 hours. The excess of thionyl chloride was removed under reduced pressure to give a yellow oil. This was taken up in pyridine (20 ml) and heated with methanesulphonamide (0.48 g) for 2 hours at 100° C. The pyridine was then removed under reduced pressure. The residue was taken up in toluene, which was removed under reduced pressure. The residue was dissolved in chloroform and the solution washed successively with water, hydrochloric acid (2 M) and water. The chloroform solution was dried and evaporated to give the sulphonamide (compound no 7) with a melting point of 104°–105° C.

EXAMPLE 6

This Example illustrates the preparation of compounds 8 to 12 inclusive of Table I.

Compounds 8 to 12 were prepared by the procedures described in paragraph (g) of Example 4, using in each case the appropriate alkanesulphonamide in place of methanesulphonamide.

EXAMPLE 7

This Example illustrates the preparation of compound no 15 of Table I.

Compound no 6 (1.0 g) was dispersed in ether (100 ml) and diazomethane in ether (about 35 ml of ether containing about 0.3 diazomethane) was added. The mixture was left overnight and the excess of diazomethane was removed by passing a stream of air through the solution. The ether was evaporated to give an oil (1.1 g). This was chromatographed on a thin layer of silica gel using a mixture of chloroform, petroleum (b.p. 60°–80° C.) and ethyl acetate in the proportions 75:20:5 by volume as the solvent. Two bands appeared; the upper band contained an unstable compound which was decomposing during the chromatography. The lower band afforded an oil identified by its mass spectrum and NMR spectrum as compound no 13 of Table I.

EXAMPLE 8

This Example illustrates the preparation of compound no 14 of Table I, that is to say, N-methanesulphonyl-2-[4-(3-chloro-5-chlorodifluoromethyl-2-pyridyloxy)-phenoxy]propionamide.

(a) Preparation of propyl
2-[4-(3-chloro-5-chlorodifluoromethyl-2-pyridyloxy)-
phenoxy]propionate 2,3-Dichloro-5-chlorodifluoromethylpyridine prepared as described in Example 4 paragraph (b) (13.92 g) was heated under reflux with propyl 2-(4-hydroxyphenoxy)propionate (13.44 g) and potassium carbonate (16.8 g) in methyl ethyl ketone for 5 hours. The mixture was cooled and filtered and the filtrate evaporated to give the propyl ester (20 g).

(b) Preparation of compound no 14

The propyl ester (20 g) from paragraph (a) above was dissolved in isopropanol (200 ml) and sodium hydroxide solution (1 g NaOH per 100 ml, 190 ml) was added dropwise over a period of 1 hour. The solution was stirred at room temperature for 5 hours, and then left overnight. The isopropanol was evaporated off under reduced pressure and the aqueous solution acidified with 2-molar hydrochloric acid. The mixture was extracted with ether (3×250 ml). The ether extracts were dried and evaporated to give an oil which crystallised on trituration with toluene and petroleum (b.p. 40°–60° C.), to give 2-[4-(3-chloro-5-chlorodifluoromethylpyridyl-2-oxy)phenoxy]propionic acid (15.5 g) with a melting point of 95°–96° C. The acid so prepared (1.5 g) was heated under reflux with stirring in thionyl chloride (30 ml) for 2½ hours. The excess of thionyl chloride was removed under reduced pressure to leave the acid chloride. This acid chloride (1.5 g) was heated under reflux with methanesulphonamide (0.38 g) in dry pyridine (20 ml) for 5 hours. The mixture was cooled and the excess of pyridine removed under reduced pressure. The residue was dissolved in water and acidified with 2-molar hydrochloric acid. The mixture was extracted with ether (150 ml). The ether extracts were washed with water (2×100 ml), dried, and evaporated. The residue was recrystallized from a mixture of toluene and petroleum (b.p. 60°–80° C.) to give the methanesulphonamide derivative (compound no 14) with a melting point of 89°–90° C.

EXAMPLE 9

This Example illustrates the preparation of N-methanesulfonyl-2-[4-(5-iodopyrimidin-2-yloxy)-phenoxy]propionamide (compound no 15 of Table I).

(a) Preparation of methyl
2-[4-(5-iodopyrimidinyl-2-oxy)phenoxy]propionate

2-Chloro-5-iodopyrimidine (1.5 g), methyl 2-(4-hydroxyphenoxy)propionate (1.3 g) and potassium carbonate (1.0 g) were heated under reflux in methyl ethyl ketone (25 ml) for 18 hours. The solvent was removed under reduced pressure and the residue shaken with water and chloroform. The chloroform layer was dried and evaporated to give an oil, which was purified by passage through silica gel (80 g) in chloroform solution. Evaporation of the chloroform gave a colourless oil identified by its NMR spectrum as the required ester.

(b) Preparation of
2-[4-(5-iodopyrimidinyl-2-oxy)phenoxy]propionic acid

The ester (1.0 g) prepared as in (a) above was dispersed in isopropanol (20 ml) and stirred while sodium hydroxide solution (10.0 ml of a solution containing 1 g NaOH per 100 ml) was added dropwise at room temperature. The mixture was left for two days, evaporated to half its volume under reduced pressure, acidified with 2-molar hydrochloric acid and extracted with ether (150 ml). The ether extracts gave a solid (0.9 g) identified as the required acid.

(c) Preparation of sulphonamide derivative

The foregoing acid (0.9 g) was heated under reflux in thionyl chloride (15 ml) with stirring for 2 hours and the excess of thionyl chloride then removed under reduced pressure. The residue was diluted with pyridine (5 ml) and heated under reflux with methanesulphonamide (0.24 g) with stirring for 7 hours. The excess of pyridine was removed under reduced pressure and the residue diluted with ice water and acidified with 2-molar hydrochloric acid. The mixture was extracted with chloroform. The extracts were dried and evaporated and the residue triturated with ether. The solid so obtained was recrystallised from isopropanol using decolourising charcoal, to give the sulphonamide derivative (compound no 15 of Table I) (0.3 g) with a melting point of 167°–169° C.

EXAMPLE 10

This Example illustrates the herbicidal properties of the compounds used in the process of the invention. Each compound was formulated for test by mixing an appropriate amount of it with 5 ml of an emulsion prepared by diluting 160 ml of a solution containing 21.8 grams per liter of Span 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar proportions of ethylene oxide with sorbitan monooleate. The mixture of the compound and the emulsion was shaken with glass beads and diluted to 40 ml with water.

The spray composition so prepared was sprayed on to young pot plants (post-emergence test) of the species named in Table II below, at a rate equivalent to 1000 liters per hectare. Damage to plants was assessed 14 days after spraying by comparison with untreated plants, on a scale of 0 to 5 where 0 is 0 to 20% kill and 5 represents 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5. The results are given in Table II below. A dash (—) means that no test was made.

TABLE II

| COMPOUND NO | A | B | Sb | Rp | Ct | Sy | Mz | Ww | Rc | Sn | Ip | Am | Pi | Ca | Po | Xa | Ab | Cv | Ot | Dg | Pu | St | Ec | Sh | Ag | Cn |
|---|---|---|---|---|---|---|---|---|---|---|---|---|---|---|---|---|---|---|---|---|---|---|---|---|---|---|
| 1 | Pre | 1 | 1 | 0 | 0 | 0 | 5 | 3 | 5 | 0 | 0 | 0 | 0 | 0 | 0 | 0 | 0 | — | 4 | — | 5 | 5 | 5 | 5 | 5 | 0 |
|  | Post | 1 | 2 | 1 | 0 | 0 | 5 | 0 | 3 | 0 | 0 | 0 | 0 | 0 | 0 | 0 | 0 | 5 | 5 | 2 | 5 | 5 | 5 | 0 | 0 | 0 |

TABLE II-continued

| COMPOUND NO | A | B | Sb | Rp | Ct | Sy | Mz | Ww | Rc | Sn | Ip | Am | Pi | Ca | Po | Xa | Ab | Cv | Ot | Dg | Pu | St | Ec | Sh | Ag | Cn |
|---|---|---|---|---|---|---|---|---|---|---|---|---|---|---|---|---|---|---|---|---|---|---|---|---|---|---|
| 1 | Pre | 5 | 0 | 0 | 0 | 0 | 5 | 3 | 5 | 2 | 0 | 0 | 0 | 2 | 0 | 0 | 0 | — | 4 | — | 5 | 5 | 5 | 5 | 4 | 0 |
|  | Post | 5 | 2 | 1 | 0 | 0 | 5 | 2 | 3 | 0 | 0 | 0 | 0 | 0 | 0 | 0 | 0 | 0 | 4 | 5 | 4 | 4 | 5 | 5 | 0 | 0 |
| 2 | Pre | 1 | 0 | 0 | 0 | 0 | 5 | 3 | 5 | 0 | 0 | 0 | 0 | 0 | 0 | 5 | 0 | — | 4 | — | 5 | 5 | 5 | 4 | 4 | 0 |
|  | Post | 1 | 0 | 0 | 0 | 0 | 5 | 0 | 3 | 0 | 0 | 0 | 0 | 0 | 0 | 0 | 0 | 0 | 3 | 4 | 3 | 5 | 5 | 5 | 0 | 0 |
| 3 | Pre | 1 | 0 | 0 | 0 | 0 | 5 | 4 | 5 | 0 | 0 | 1 | — | — | 1 | 0 | 0 | — | 4 | — | 5 | 5 | 5 | 4 | 5 | 0 |
|  | Post | 1 | 1 | 0 | 0 | 0 | 5 | 4 | 4 | 0 | 0 | 0 | 3 | 3 | 1 | 1 | 1 | 0 | 4 | 5 | 3 | 5 | 5 | 5 | 4 | 0 |
| 4 | Pre | 1 | 0 | 0 | 0 | 0 | 4 | 4 | 5 | 0 | 0 | 4 | — | 4 | 2 | 0 | 1 | — | 4 | — | 4 | 5 | 5 | 4 | 5 | 0 |
|  | Post | 1 | 0 | 0 | 0 | 0 | 5 | 5 | 2 | 0 | 0 | 0 | 0 | 2 | 1 | 0 | 0 | 0 | 4 | 4 | 1 | 5 | 5 | 5 | 3 | 0 |
| 4 | Pre | 5 | 1 | 0 | 2 | 0 | 5 | 5 | 5 | 1 | 0 | 4 | — | 4 | 3 | 0 | 3 | — | 4 | — | 5 | 5 | 5 | 5 | 5 | 0 |
|  | Post | 5 | 1 | 2 | 1 | 0 | 5 | 5 | 4 | 0 | 0 | 4 | 2 | 3 | 0 | 0 | 0 | 0 | 4 | 5 | 4 | 5 | 5 | 5 | 4 | 0 |
| 5 | Pre | 1 | 4 | 1 | 0 | 0 | 4 | 0 | 5 | 0 | 0 | 4 | — | 4 | 5 | — | 0 | — | 4 | — | 4 | 4 | 5 | 2 | 0 | 0 |
|  | Post | 1 | 1 | 1 | 0 | 0 | 4 | 0 | 2 | 0 | 0 | 2 | 0 | 1 | 1 | 0 | 0 | 0 | 0 | 3 | 0 | 5 | 5 | 1 | 1 | 0 |
| 5 | Pre | 5 | 4 | 1 | 0 | 0 | 5 | 3 | 5 | 0 | 0 | 4 | — | 4 | 3 | 0 | 0 | — | 4 | — | 4 | 5 | 5 | 4 | 1 | 0 |
|  | Post | 5 | 1 | 3 | 2 | 0 | 5 | 0 | 3 | 0 | 0 | 4 | 0 | 2 | 2 | 0 | 0 | 0 | 1 | 4 | 0 | 5 | 5 | 3 | 0 | 0 |
| 6 | Pre | 0.02 | 0 | 0 | — | 0 | 1 | 1 | 2 | 0 | 1 | 1 | 0 | 0 | 0 | 0 | 0 | — | 1 | 3 | 2 | 3 | 2 | 2 | 0 | 0 |
|  | Post | 0.02 | — | 1 | 0 | 0 | 4 | 0 | 0 | 0 | 0 | 0 | 0 | — | 1 | — | 0 | 0 | 0 | — | 0 | 3 | 4 | 4 | 0 | 0 |
| 6 | Pre | 0.08 | 0 | 0 | 0 | 0 | 3 | 4 | 3 | 1 | 0 | 0 | 0 | 0 | — | 0 | 1 | — | 3 | 4 | 3 | 4 | 4 | 3 | 1 | 0 |
|  | Post | 0.08 | 0 | 1 | 0 | 0 | 4 | 2 | 3 | 0 | 0 | 0 | 0 | 0 | 0 | — | 0 | 0 | 1 | — | 2 | 4 | 5 | 4 | 0 | 0 |
| 7 | Pre | 0.02 | 0 | 0 | 0 | 0 | 1 | 0 | 0 | — | 0 | 0 | 0 | 0 | 0 | — | — | — | 0 | 1 | 0 | 2 | 1 | 1 | 0 | 0 |
|  | Post | 0.02 | 0 | 0 | — | 0 | 3 | 1 | 1 | 0 | 0 | 0 | 0 | 0 | 0 | — | 0 | 0 | 0 | — | 0 | 0 | 4 | 3 | 0 | 0 |
| 7 | Pre | 0.08 | 0 | 0 | 0 | 0 | 3 | 1 | 3 | 0 | 0 | 1 | — | 0 | 0 | 0 | 0 | — | 0 | 1 | 0 | 2 | 1 | 1 | 0 | 0 |
|  | Post | 0.08 | 0 | 0 | 0 | 0 | 3 | 2 | 1 | 0 | 0 | 0 | 0 | 0 | 0 | — | 0 | 0 | 0 | — | 0 | 0 | 4 | 4 | 1 | 0 |

The names of the test plants were as follows:
Sb Sugar beet
Rp Rape
Ct Cotton
Sy Soya bean
Mz Maize
Ww Winter wheat
Rc Rice
Sn *Senecio vulgaris*
Ip *Ipomoea purpurea*
Am *Amaranthus retroflexus*
Pi *Polygonum aviculare*
Ca *Chenopodium album*
Po *Portulaca oleracea*
Xa *Xanthium pensylvanicum*
Ab *Abutilon theophrastii*
Cv *Convolvulus arvensis*
Ot Cultivated oats and wild oats (*Avena fatua*)
  Wild oats are used in the post-emergence test and cultivated oats in the pre-emergence test
Dg *Digitaria sanguinalis*
Pu *Poa annua*
St *Setaria viridis*
Ec *Echinochloa crus-galli*
Sh *Sorghum halepense*
Ag *Agropyron repens*
Cn *Cyperus rotundus*

EXAMPLE 11

This Example illustrates the herbicidal properties of the compounds used in the process of the invention. Each compound (0.12 g) was formulated for test by mixing it with 5 ml of an emulsion prepared by diluting 100 ml of a solution containing 21.8 grams per liter of Span 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar proportions of ethylene oxide with sorbitan mono-oleate. The mixture of the compound and the emulsion was shaken with glass beads and diluted to 12 ml with water.

The spray composition so prepared was sprayed on to young pot plants (post-emergence test) of the species named in Table III below, at a rate equivalent to 1000 liters per hectare (10 kilograms of test compound per hectare). Damage to plants was assessed 14 days after spraying by comparison with untreated plants, on a scale of 0 to 3 where 0 is no effect and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the sme scale of 0 to 3. The results are given in Table III below:

TABLE III

| COMPOUND NO | RATE OF APPLICATION KG/HA | PRE- OR POST- EMERGENCE APPLICATION | TEST PLANTS | | | | | |
|---|---|---|---|---|---|---|---|---|
| | | | Lt | To | Ot/Av | Ll | Cn | St |
| 1 | 10.0 | Pre | 2 | 1 | 3 | 3 | 0 | 3 |
|  |  | Post | 2 | 2 | 3 | 3 | 0 | 3 |
| 2 | 1.0 | Pre | 0 | 0 | 3 | 3 | 0 | 3 |
|  |  | Post | 0 | 0 | 3 | 3 | 0 | 3 |
| 3 | 10.0 | Pre | 3 | 1 | 3 | 3 | 0 | 3 |
|  |  | Post | 1 | 1 | 3 | 3 | 0 | 3 |
| 4 | 10.0 | Pre | 2 | 2 | 3 | 3 | 0 | 3 |
|  |  | Post | 1 | 1 | 3 | 3 | 0 | 3 |
| 5 | 10.0 | Post | 0 | 0 | 2 | 3 | 0 | 3 |
|  |  | Post | 0 | 0 | 0 | 2 | 0 | 3 |
| 14 | 0.2 | Pre | 1 | 0 | 2 | 3 | 0 | 3 |
|  |  | Post | 0 | 0 | 3 | 2 | — | 3 |

The names of the test plants are as follows:
Lt Lettuce
To Tomato
Ot/Av Cultivated oats and wild oats (*Avena fatua*).
  Wild oats are used in the post-emergence test and cultivated oats in the pre-emergence test.
Ll *Lolium perenne* (perennial rye grass)
Cn *Cyperus rotundus*
St *Setaria viridis*

EXAMPLE 12

This Example illustrates a composition according to the invention comprising a dispersible powder.

The following ingredients were ground together to form a finely divided powder.

| Constituent | Percentage by weight |
|---|---|
| Compound no 6 | 50 |
| Vanisperse CB | 5 |
| Aerosol OTB | 2 |
| China clay GT-Y | to 100 percent |

Vanisperse CB comprises sodium lignosulphonate. Aerosol OTB comprises dioctylsulphosuccinate.

EXAMPLE 13

This Example illustrates a composition according to the invention comprising an aqueous dispersion. The following ingredients were ground together to give an aqueous dispersion.

| Constituent | Pecentage by weight |
|---|---|
| Compound no 7 | 50 |
| Synperonic NP13 | 1.25 |
| Polyfon H | 5 |
| Water | to 100 percent |

Synperonic NP13 comprises a condensate of p-nonyl phenol with 13 molar proportions of ethylene oxide. Polyfon H comprises sodium lignosulphonate.

Where the group $R^3$ is a hydrogen atom, the compounds of the invention are in principle capable of existing in a tautomeric form in which this hydrogen atom is attached not to the nitrogen atom, but to the oxygen atom of the adjacent carbonyl group, with consequent rearrangement of the chemical bonds of the molecule. This tautomeric form is shown in the formula below:

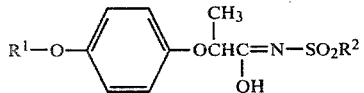

The structural formulae given in this specification for compounds of the invention wherein $R^3$ is hydrogen are intended to be inclusive of and representative of such possible tautomeric forms. The structural formulae are also intended to include physically distinguishable modifications of the compounds which may arise, for example, from different ways in which the molecules are arranged in a crystal lattice, or from the inability of parts of the molecule to rotate freely in relation to other parts, or from geometrical isomerism, or from intramolecular or inter-molecular hydrogen bonding, or otherwise.

The compounds of the invention may be used in admixture with other herbicides. Accordingly the invention further provides a herbicidal composition comprising a mixture of at least one herbicide of formula (I) above with at least one other herbicide.

The other herbicide may be any herbicide not having the formula (I). It may be a herbicide having a similar spectrum of herbicidal effect, that is to say a herbicide mainly effective against grasses, or it may be a herbicide having a complementary action, for example a herbicide that is active against broad-leaved weeds.

Examples of herbicides which may be mixed with the compounds of the invention include the following:

A. Bipyridylium herbicides, for example paraquat dichloride (1,1'-dimethyl-4,4'-bipyridylium dichloride) and diquat dibromide (1,1'-ethylene-2,2'-bipyridylium dibromide).

B. Glyphosate (N-phosphoromethylglycine) and its salts and esters.

C. Bentazon (3-isopropyl-(1H)-benzo-2,1,3-thiazine-4-one 2,2-dioxide).

D. Hormone herbicides
  e.g. MCPA (4-chloro-2-methylphenoxyacetic acid)
  2,4-D (2,4-dichlorophenoxyacetic acid)
  Dichlorprop (2-[2,4-dichlorophenoxy]propionic acid)
  2,4,5-T (2,4,5-trichlorophenoxyacetic acid) Mecoprop (2-[4-chloro-2-methylphenoxy]propionic acid).

E. Urea herbicides
  e.g. Chloroxuron (3-[4-(4-chlorophenoxy)phenyl]-1,1-dimethyl urea)
  Diuron (1-[3,4-dichlorophenyl]-3,3-dimethyl urea)
  Fluometuron (1-[metatrifluoromethylphenyl]3,3-dimethyl urea).

F. Triazine herbicides
  e.g. simazine (2-chloro-4,6-diethylamino-1,3,5-triazine)
  atrazine (2-chloro-4-ethylamino-6-isopropylamino-1,3,5-triazine)

G. 1-alkoxy-1-alkyl-3-phenylurea herbicides
  e.g. linuron (3[3,4-dichlorophenyl]-1-methoxy-1-methyl urea)
  monolinuron (3-[4-chlorophenyl]-1-methoxy-1-methyl urea).

H. 1,2,4-Triazine-5-one herbicides
  e.g. metamitron (4-amino-4,5-dihydro-3-methyl-6-phenyl-1,2,4-triazin-5-one)
  metribuzin (4-amino-6-tertbutyl-4,5-dihydro-3-methylthio-1,2,4-triazin-5-one).

I. Anilide herbicides
  e.g. butachlor (N-butoxymethyl-α-chloro-2',6'-diethylacetanilide)
  alachlor (N-methoxymethyl-α-chloro-2',6'-diethylacetanilide)
  and propanil (3,4-dichloropropionanilide).

J. Haloalkanoic acids
  e.g. dalapon (2,2-dichloropropionic acid)
  TCA (trichloroacetic acid)

K. Diphenyl ether herbicides
  e.g. fluorodifen (4-nitrophenyl 2'-nitro-4'-trifluoromethylphenyl ether)
  2-nitro-5-(2-chloro-4-trifluoromethylphenoxy)benzoic acid
  and 2-chlorophenyl-3'-ethoxy-4'-nitro-4-trifluoromethylphenyl ether The mixtures of the invention generally contain from 0.1 to 10 parts, conveniently from 0.2 to 2 parts by weight of herbicide of formula (I) per part by weight of the other herbicide, depending upon the relative activity of the components. The amount of the mixture to be applied will depend upon a number of factors, for example the particular plant species to which the mixture is to by applied, but in general an amount of from 0.1 to 5.0 kilograms per hectare will usually be suitable.

We claim:

1. A herbicidal sulphonamide compound of the formula (I):

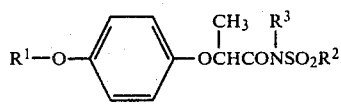

and salts thereof, wherein $R^1$ is a pyridyl group of the formula:

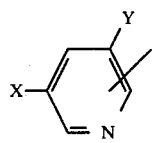

wherein the group X of the pyridyl group represents a fluorine, chlorine, bromine, or iodine atom, or an alkyl radical of 1 to 4 carbon atoms optionally substituted by one or more fluorine or chlorine atoms, and the group Y represents hydrogen, fluorine chlorine, bromine, or iodine or an alkyl radical of 1 to 4 carbon atoms optionally substituted by one or more fluorine or chlorine atoms; $R^2$ represents an alkyl radical of 1 to 6 carbon atoms optionally substituted by one or more fluorine atoms; and $R^3$ is hydrogen or an alkyl radical of 1 to 4 carbon atoms.

2. A herbicidal sulphonamide compound as claimed in claim 1 wherein the group $R^3$ is a hydrogen atom.

3. A herbicidal sulphonamide compound as claimed in claim 1 or claim 2 wherein the group $R^2$ is a methyl radical.

4. A herbicidal sulphonamide compound as claimed in claim 1 wherein the group $R^1$ is a 3,5-dichloro-2-pyridyl, 5-chloro-2-pyridyl, 3-chloro-5-trifluoromethyl-2-pyridyl, or 5-trifluoromethyl-2-pyridyl radical, $R^2$ is a methyl radical and $R^3$ is a hydrogen atom; and salts thereof.

* * * * *